United States Patent
Schuren et al.

(10) Patent No.: US 7,964,625 B2
(45) Date of Patent: Jun. 21, 2011

(54) ANTIBIOTICS COMPRISING BIS(1-ARYL-5-TETRAZOLY1)METHANE DERIVATIVES

(75) Inventors: Frank Henri Johan Schuren, Veenendaal (NL); Henricus Matheus Wilhelmus Maria Thijssen, Houten (NL); Roy Christiaan Montijn, Amsterdam (NL)

(73) Assignee: Nederlandse Organisatie Voor Toegepast-Natuurwetenschappelijk Onderzoek Tno, Vk Delft (NL)

( * ) Notice: Subject to any disclaimer, the term of this patent is extended or adjusted under 35 U.S.C. 154(b) by 418 days.

(21) Appl. No.: 12/088,299

(22) PCT Filed: Sep. 29, 2006

(86) PCT No.: PCT/NL2006/000489
§ 371 (c)(1),
(2), (4) Date: Jun. 12, 2008

(87) PCT Pub. No.: WO2007/037685
PCT Pub. Date: Apr. 5, 2007

(65) Prior Publication Data
US 2008/0280964 A1    Nov. 13, 2008

(30) Foreign Application Priority Data

Sep. 30, 2005   (EP) .................................. 05077244

(51) Int. Cl.
*A61K 31/41* (2006.01)
*C07D 257/04* (2006.01)

(52) U.S. Cl. ........................................ 514/381; 548/250

(58) Field of Classification Search .................. 548/250; 514/381
See application file for complete search history.

(56) References Cited

U.S. PATENT DOCUMENTS 2,713,581 A    7/1955    Pannone et al.

OTHER PUBLICATIONS

Shivanyuk, A. F. et al "Synthesis of bistetrazoles from N,N'-diaryl-2,2-dichloromalonimidoyl chlorides" Chemical Abstract Service, Columbus Ohio; Jan. 11, 1987 Accession No. 1987:4946.

Reidalova, L. I. et al: "Growth-regulating activity of some substituted derivatives of quinoline, bis(tetrazolyl) methane and dichloromethane" Chemical Abstract Service, Columbus Ohio; Dec. 24, 1988 Accession No. 1988: 624618.

Shivanyuk, A. F. et al "Reactivity of bis(1-aryl-5-tetrazolyl)dichloromethanes" Chemical Abstract Service, Columbus Ohio; Feb. 8, 1992 Accession No. 1992:41375.

*Primary Examiner* — Golam M Shameem
(74) *Attorney, Agent, or Firm* — Lucas & Mercanti,LLP

(57) ABSTRACT

The invention relates to the field of antibiotic compositions, both inside and outside the medical field. Presented is a new class of antibiotic compounds, the bis(1-aryl-5-tetrazolyl) methanes, which are especially useful for combating infections with gram-positive bacteria and especially MRSA.

6 Claims, 1 Drawing Sheet

ANTIBIOTICS COMPRISING BIS(1-ARYL-5-TETRAZOLY1)METHANE DERIVATIVES

CROSS-REFERENCE TO RELATED APPLICATIONS

Figure 1:
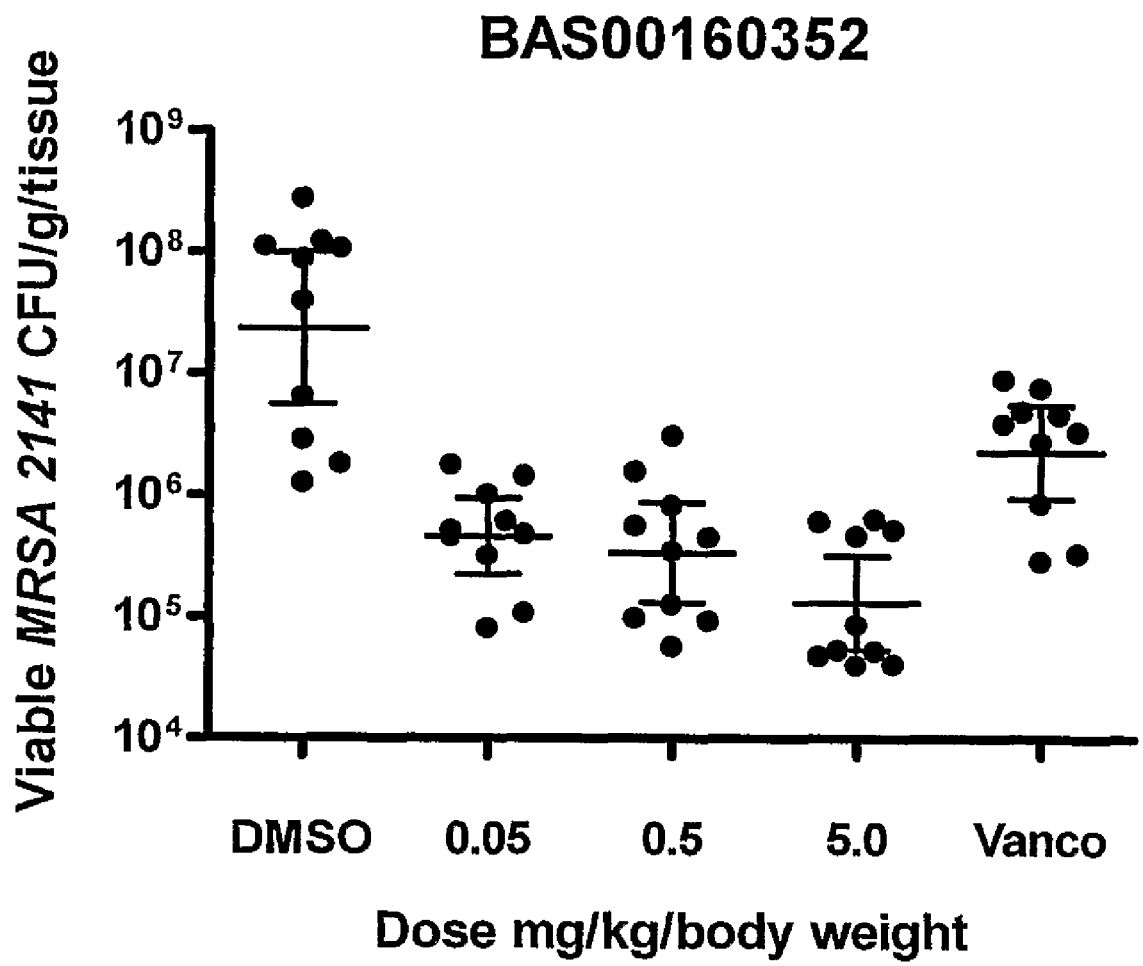

This application is a 371 of PCT/NL2006/000489 filed on Sep. 29, 2006, which claims the benefit of European Application No. EP 05077244.1 filed on Sep. 30, 2005, the contents of each of which are incorporated herein by reference.

The invention relates to the field of pharmaceutical compounds, especially antibiotic compounds.

Searching for novel antibiotic compounds has become more and more important, especially since many micro-organisms are becoming resistant to known antibiotic compounds. This is especially the case for a group of *Staphylococcus aureus* bacteria, which are now identified as MRSA (methicillin-resistant *S. aureus*). Therefore, there is an ever increasing need for new antibiotic compounds, which can be used against micro-organisms that have become resistant to commonly used antibiotics.

The present inventors have developed a new test and detection system to search for novel antibiotics and novel targets for antibiotics. This system is the subject of several copending applications (WO 03/0087397, WO 03/0981389, WO 05/0035782, WO 05/106033). Using this system now a new class of antibiotics has been uncovered.

The presently disclosed new class of antibiotics covers compounds with the general formula (I):

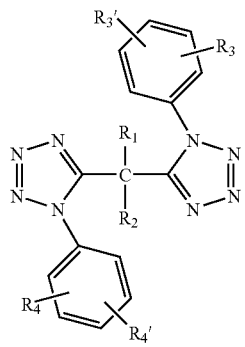

wherein $R_1$ and $R_2$ are each independently halogen, lower alkyl or absent, with the proviso that $R_1$ and $R_2$ are not both absent, and wherein $R_3$, $R_3'$, $R_4$ and $R_4'$ are each independently absent, OH, $SO_2NH_3$, lower alkyl, lower alkoxy, lower alkoxy (methyl), aryl, heteroaryl, wherein the alkyl, alkoxy, aryl and heteroaryl may be substituted, arylalkoxy or halogen.

The term "alkyl" or "lower alkyl" refers to a straight or branched alkyl radical containing one to six carbon atoms including, but not limited to, methyl, ethyl, propyl, isopropyl, n-butyl, t-butyl and neopentyl.

The term "loweralkoxy" refers to an alkyl or loweralkyl group as previously defined, i.e. with one to six C atoms, attached to a parent molecular moiety by an ether linkage.

The term "loweralkoxy (methyl)" refers to an alkoxy group as described above attached to a parent molecular moiety via a methylene group (—$CH_2$—).

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, substituted loweralkyl, haloalkyl, alkoxy, thioalkoxy, amino, alkylamino, dialkylamino, acylamino, benzyloxycarbonyl, cyano, hydroxyl, halo, mercapto, nitro, carboxaldehyde, carboxy, alkoxycarbonyl, carboxamide, and protected hydroxyl. In addition, substituted aryl groups include tetrafluorophenyl and pentafluorophenyl.

The term "heteroaryl", as used herein, refers to a mono- or bicyclic fused aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "substituted alkyl or alkoxy" as used herein refers to an alkyl or alkoxy group as defined herein substituted by independent replacement of one, two or three of the hydrogen atoms thereon with Cl, Br, F, I, OH, CN, haloalkyl, thioalkoxy, amino, alkylamino, dialkylamino, mercapto, nitro, carboxaldehyde, carboxy, alkoxycarbonyl and carboxamide.

The term "substituted aryl" as used herein refers to an aryl group as defined herein substituted by independent replacement of one, two or three of the hydrogen atoms thereon with Cl, Br, F, I, OH, CN, $C_1$-$C_3$-alkyl, $C_1$-$C_6$-alkoxy, $C_1$-$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group. Also, substituted aryl groups include tetrafluorophenyl and pentafluorophenyl.

The term "substituted heteroaryl" as used herein refers to a heteroaryl group as defined herein substituted by independent replacement of one, two or three of the hydrogen atoms thereon with Cl, Br, F, I, OH, CN, $C_1$-$C_3$-alkyl, $C_1$-$C_6$-alkoxy, $C_1$-$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

The term "pharmaceutically acceptable salts" as used herein refers to those carboxylate salts, esters, and prodrugs of the compound of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

Pharmaceutically acceptable salts are well known in the art and refer to the relatively non-toxic, inorganic and organic acid addition salts of the compounds of the present invention. For example, S. M. Berge, et al. describe pharmaceutically acceptable salts in detail in J. Pharmaceutical Sciences, 66: 1-19 (1977) which is incorporated herein by reference. The salts can be prepared in situ during the final isolation and purification of the compounds of the invention, or separately by reacting the free base function with a suitable organic acid.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulphate, tartrate, thiocyanate, p-toluenesulphonate, undecanoate, valerate salts, and the like. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate. sulphate, phosphate, nitrate, lower-alkyl sulphonate and aryl sulphonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable solvate" represents an aggregate that comprises one or more molecules of the solute, such as a compound of the invention, with one or more molecules of solvent.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

Preferred compounds according to formula (I) are those compounds in which one or both of $R_1$ and $R_2$ is Cl. Also preferred are compounds according to formula (I) wherein $R_3$ and $R_4$ are located at the ortho position of the phenyl moieties and $R_3'$ and $R_4'$ are absent. Most preferred is a compound, wherein $R_1=R_2=Cl$, $R_3=R_4=CH_3$ and $R_3'$ and $R_4'$ are absent and wherein $R_3$ and $R_4$ are in the ortho position.

In general, a synthetic route for (several of) the compounds according to formula (I) has been presented by Shivanyuk, A. F. et al., (1986) Zhurnal Organicheskoi Chimii 22(1):200-205, while the electronic structure of these molecules has been provided in Pen'kovskii et al., (1991) Zhurnal Organicheskoi Chimii 27(1):148-153. In short (see Scheme 1), synthesis starts from malonic acid di-esters (ROC(O)CC(O)OR) which are converted, in the present case with aniline or derivatives thereof, to the corresponding diamide (RNHC(O)CC(O)NHR) which are subsequently reacted with $PCl_5$ to a chlorinated imidoyl chloride derivative. After reaction with sodium azide the tetrazole derivatives are isolated Scheme 1:

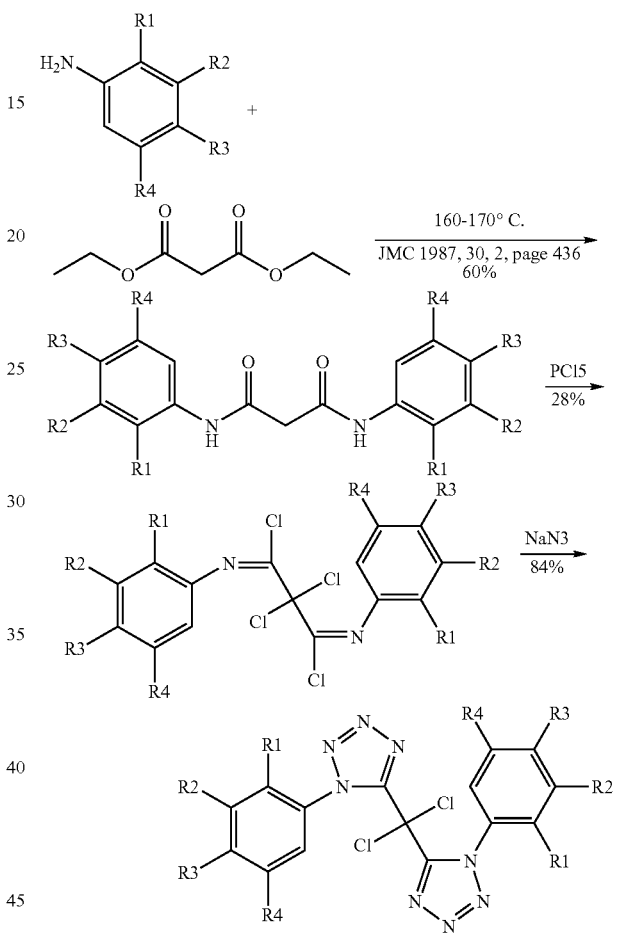

The amidation reaction has been described by Vennerstrom, J. L. and Holmes, T. J. Jr., (1987) J. Med. Chem. 30: 434-437).

Asymmetric compounds, i.e. where the R-groups at the phenyl rings are not identical can be made by reacting two different aniline derivatives with the malonic acid di-esters (Scheme 2):

Scheme 2:

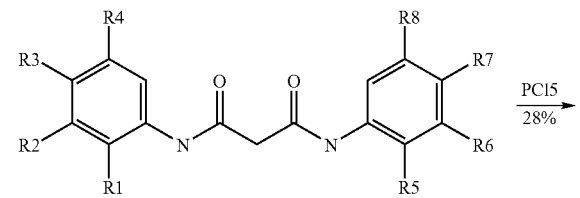

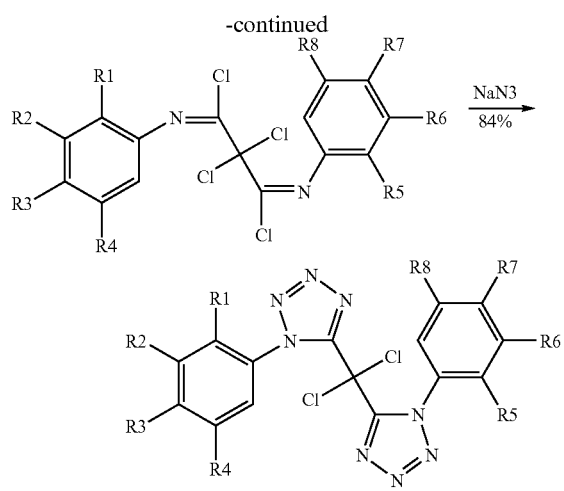

The compounds according to formula (I) have antibiotic activity, in particular against Gram positive bacteria. They are especially active against staphylococcal and enterococcal strains, and in particular against *S. aureus*, including also the strains of *S. aureus*, that are commonly known as MRSA strains.

They can be used in pharmaceutical compositions for the treatment of bacterial diseases, especially those diseases caused by the above mentioned micro-organisms, or in conditions wherein the subject runs the risk of being infected with micro-organisms.

The compounds of the invention or compositions therewith can, however, also be used in other than pharmaceutical applications, e.g. in cosmetics (e.g. for the treatment of acne), in detergents and/or other cleaning solutions, in anti-fouling paints, in food or feed or in food or feed packaging, and so on.

A compound according to the formula (I), or a pharmaceutically acceptable salt or prodrug thereof, may be provided to a subject in need thereof for prophylactic or therapeutic reasons. A compound according to the formula (I), or a pharmaceutically acceptable salt or prodrug thereof, may be provided to a subject in need thereof in the form of any pharmaceutical preparation, when such administration form is capable of treating and/or preventing infection in a subject. As a consequence of the prevention or treatment of infection, also the clinical effects or sequellae of infection will be prevented.

The present invention also relates to a method for preventing and/or treating infection in a subject, preferably a human or other mammalian subject, said method comprising administering to said subject a therapeutically and/or prophylactically effective amount of a pharmaceutical composition comprising a compound according to formula (I), more preferably a compound as depicted in Table I, or pharmaceutically acceptable salts or prodrugs thereof and a pharmaceutically acceptable carrier, and optionally one or more excipients.

The present invention also relates to the use of a compound according to formula (I), more preferably a compound as depicted in Table I or pharmaceutically acceptable salts or prodrugs thereof for the manufacture of a medicament for treating infection, preferably bacterial infections, most preferably staphylococcal or enterococcal infection.

An antibiotic therapy (i.e. the method for preventing and/or treating infection in a subject) may also comprise administering to an otherwise healthy individual, at risk of developing infection, a prophylactically effective amount of the pharmaceutical composition.

Dosages for achieving the antibiotic effects of the pharmaceutical composition described herein may easily be determined by the skilled person. For purposes of the present invention, an effective dose will be a daily dose between about 0.01 mg and 10 grams of the compound according to formula (I) for an adult human being. More preferably a dose between 0.1 mg and 1 gram is used, even more preferably a dose of 1 mg-100 mg and most preferably a dose of 4-40 mg of the compound of the invention is administered. This daily dose may be given as a one-dose administration, or it may be subdivided in several subdoses, which are administered spread over the day.

For oral administration, the compositions may be packed in e.g. gelatin capsules or may be tableted in the form of tablets. For oral therapeutic application the active compound may be administered with excipients and e.g. used in the form of powders, sachets, tablets, pills, pastilles or capsules. The pharmaceutical compositions may be prepared by conventional means with pharmaceutically acceptable excipients such as binding agents (e.g. pregelatinised maize starch, tragacanth gum, gelatine, polyvinylpyrrolidone or hydroxypropyl methylcellulose); fillers (e.g. lactose, microcrystalline cellulose, mannitol or calcium hydrogen phosphate); lubricants (e.g. magnesium stearate, talc or silica); disintegrants (e.g. potato starch, sodium starch glycollate or alginate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

The compounds according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

When dosing is in the form of a capsule, the capsule may comprise apart from the elements mentioned above a liquid carrier such as an oil. Dosage form may further be provided with coatings of sugar, shellac or other agents. The components of the pharmaceutical composition are preferably chosen such that they do not reduce the desired working of the active compound.

The pharmaceutical compositions can further comprise flavoring sweetening, coloring and/or preservative agents.

A compound according to the formula (I), or a pharmaceutically acceptable salt or prodrug thereof may also be administered in the form of e.g. an elixir, a suspension, a syrup, a waffle or a chewing gum.

In a pharmaceutical composition as described above, a compound according to the formula (I), or a pharmaceutically acceptable salt or prodrug thereof, is used in an amount of from 0.01 to 99.9% by weight, preferably from 0.01 to 10 wt. %, and more preferably from 0.05 to 5 wt. %.

The present invention further relates to a method for the preparation of a pharmaceutical composition for preventing and/or treating infection, comprising processing or incorporating a compound according to the formula (I), or a pharmaceutically acceptable salt or prodrug thereof, as an active substance, together with a pharmaceutically acceptable carrier in a pharmaceutical composition.

The preparation of a pharmaceutical composition may very suitably occur by mixing all separate ingredients such as fillers, binders, lubricants and optionally other excipients together with a compound according to the formula (I), or a pharmaceutically acceptable salt or prodrug thereof, and processing the mixture obtained to a pharmaceutical preparation.

TABLE I

Exemplary compounds of general formula I. For $R_3$, $R_4$, $R_3'$ and $R_4'$ is indicated whether the indicated moieties are in the para (p-), meta (m-) or ortho (o-) position

| Compound | $R_1$ | $R_2$ | $R_3$ | $R_4$ | $R_3'$ | $R_4'$ |
|---|---|---|---|---|---|---|
| BAS00160345(NewCo001) | Cl | Cl | p-Cl | p-Cl | — | — |
| BAS00096442(NewCo002) | Cl | Cl | p-CH$_3$ | p-CH$_3$ | — | — |
| BAS00160352(NewCo003) | Cl | Cl | o-CH$_3$ | o-CH$_3$ | — | — |
| BAS00096453(NewCo004) | Cl | Cl | — | — | — | — |
| F1708-0027(NewCo005) | Cl | — | p-CH$_3$ | p-CH$_3$ | — | — |
| 5364120(NewCo006) | Cl | Cl | p-O—CH$_3$ | p-O—CH$_3$ | — | — |
| NewCo007 | Cl | Cl | o-O—CH$_3$ | o-O—CH$_3$ | | |
| NewCo008 | Cl | Cl | p-CH$_3$ | p-CH$_3$ | o-CH$_3$ | o-CH$_3$ |
| NewCo009 | Cl | Cl | m-CH$_3$ | m-CH$_3$ | | |
| NewCo0010 | Cl | Cl | p-Br | p-Br | | |
| NewCo0011 | Cl | Cl | p-CF$_3$ | p-CF$_3$ | | |
| NewCo0012 | Cl | Cl | m-Cl | m-Cl | m-Cl | m-Cl |
| NewCo0013 | Cl | Cl | o-CF$_3$ | o-CF$_3$ | | |
| NewCo0014 | Cl | Cl | m-CF$_3$ | m-CF$_3$ | m-CF$_3$ | m-CF$_3$ |
| NewCo0015 | Cl | Cl | p-F | p-F | o-F | o-F |
| NewCo0016 | Cl | Cl | p-O—CF$_2$ | p-O—CF$_2$ | | |
| NewCo0017 | Cl | Cl | p-Cl | p-O—CH$_3$ | m-Cl | |
| NewCo0018 | Cl | Cl | o-F | o-F | | |
| NewCo0019 | Cl | Cl | m-Cl | m-Cl | o-Cl | o-Cl |
| NewCo0020 | Cl | Cl | p-SO$_2$NH$_2$ | p-SO$_2$NH$_2$ | | |
| NewCo0021 | Cl | Cl | p-O—CH$_3$ | p-O—CH$_3$ | m-Cl | m-Cl |
| NewCo0022 | Cl | Cl | o-O—CH$_3$ | o-O—CH$_3$ | m-Cl | m-Cl |
| NewCo0023 | Cl | Cl | m-Cl | m-Cl | o-Cl | o-Cl |
| NewCo0024 | Cl | Cl | p-CH$_3$ | p-CH$_3$ | m-CH$_3$ | m-CH$_3$ |
| NewCo0025 | Cl | Cl | p-o-phenyl | p-o-phenyl | | |
| NewCo0027 | Cl | Cl | o-O—CH$_3$ | o-O—CH$_3$ | m-Cl | m-Cl |
| NewCo0028 | Cl | Cl | m-O—CH$_3$ | m-O—CH$_3$ | m-O—CH$_3$ | m-O—CH$_3$ |
| NewCo0029 | Cl | Cl | m-CH$_3$ | m-CH$_3$ | o-CH$_3$ | o-CH$_3$ |
| NewCo0030 | Cl | | o-CH$_3$ | o-CH$_3$ | | |

The chemical names of these compounds are provided in the following list:

NewCo001: Bis-(1-p-chlorobenzen-5-tetrazolyl)-dichloromethane (CAS no. 105678-80-6 = 1H-Tetrazole,5,5'-(dichloromethylene) bis[1-(chlorophenyl)])
NewCo002: Bis-(1-p-tolyl-5-tetrazolyl)-dichloromethane (CAS no. 77174-39-1 = 1H-Tetrazole,5,5'-(dichloromethylene) bis[1-(methylphenyl)])
NewCo003: Bis-(1-o-tolyl-5-tetrazolyl)-dichloromethane (CAS no. 105678-65-7 = 1H-Tetrazole,5,5'-(dichloromethylene) bis[1-(2-methylphenyl)])
NewCo004: Bis-(1-benzene-5-tetrazolyl)-dichloromethane (CAS no. 77166-08-6 = 1H-Tetrazole,5,5'-(dichloromethylene) bis[1-(phenyl)])
NewCo005: Bis-(1-p-tolyl-5-tetrazolyl)-chloromethane (CAS no. 138352-04-2 = 1H-Tetrazole,5,5'-(chloromethylene) bis[1-(4-methylphenyl)])
NewCo006: Bis-(1-o-methoxybenzene-5-tetrazolyl)-dichloromethane (CAS no. 105678-79-3 = 1H-Tetrazole,5,5'-(dichloromethylene) bis[1-(4-methoxyphenyl)])
NewCo007: Bis-(1-o-methoxybenzene-5-tetrazolyl)-dichloromethane
NewCo008: Bis-(1-(2,4-dimethylbenzene-5-tetrazolyl)-dichloromethane
NewCo009: Bis-(1-m-methylbenzene-5-tetrazolyl)-dichloromethane
NewCo0010: Bis-(1-p-bromobenzene-5-tetrazolyl)-dichloromethane
NewCo0011: Bis-(1-trifluoromethylbenzene-5-tetrazolyl)-dichloromethane
NewCo0012: Bis-(1-(3,5-dichlorobenzene-5-tetrazolyl)-dichloromethane
NewCo0013: Bis-(1-o-trifluoromethylbenzene-5-tetrazolyl)-dichloromethane
NewCo0014: Bis-(1-(3,5-bis-trifluoromethylbenzene-5-tetrazolyl)-dichloromethane
NewCo0015: Bis-(1-(2,4-difluorobenzene-5-tetrazolyl)-dichloromethane
NewCo0016: Bis-(1-p-difluoromethoxybenzene-5-tetrazolyl)-dichloromethane
NewCo0017: 5-{dichloro[1-(3,4-dichlorophenyl)-1H-1,2,3,4-tetraazo-5-yl]methyl}-1-[4-metoxyphenyl]-1H-1,2,3,4-tetraazole
NewCo0018: Bis-(1-o-fluorobenzene-5-tetrazolyl)-dichloromethane
NewCo0019: Bis-(1-(2,5-dichlorobenzene-5-tetrazolyl)-dichloromethane
NewCo0020: Bis-(1-p-sulfonoamidobenzene-5-tetrazolyl)-dichloromethane
NewCo0021: Bis-(1-m-chloro-p-methoxybenzene-5-tetrazolyl)-dichloromethane
NewCo0022: Bis-(1-(5-chloro-2-methoxybenzene-5-tetrazolyl)-dichloromethane
NewCo0023: Bis-(1-o,m-dichlorobenzene-5-tetrazolyl)-dichloromethane
NewCo0024: Bis-(1-m,p-dimethylbenzene-5-tetrazolyl)-dichloromethane
NewCo0025: Bis-(1-p-phenoxybenzene-5-tetrazolyl)-dichloromethane
NewCo0027: Bis-(1-(3-chloro-2-methoxybenzene-5-tetrazolyl)-dichloromethane
NewCo0028: Bis-(1-(2,5-dimethoxybenzene-5-tetrazolyl)-dichloromethane
NewCo0029: Bis-(1-(2,5-dimethylbenzene-5-tetrazolyl)-dichloromethane
NewCo0030: Bis-(1-o-tolyl-5-tetrazolyl)-chloromethane.

EXAMPLES

Example 1

Synthesis of Compounds

1a. Bis-(1-o-methoxybenzene-5-tetrazolyl)-dichloromethane 100 mmol 2-methoxyaniline and 50 mmol diethyl malonate were put together and stirred overnight at 170° C. The formed ethanol was distilled off directly (100 mmol≡6.6 mL) on a stream of nitrogen. N1,N3-di(2-methoxy-phenyl)-malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 24.5 g N1,N3-di(2-methoxy-phenyl)-malonamide was obtained.

At room temperature 6.44 mmol $PCl_5$ was added to a suspension of 1.61 mmol N1,N3-di(2-methoxy-phenyl)-malonamide in 5 mL $POCl_3$. The reaction was heated at reflux for 16 hours. The progress of the reaction was followed by NMR. The reaction was cooled to room temperature and evaporated to dryness in vacuo to afford a yellow/brown oil. Solvent residues were removed by drying at 100° C. and using an oil pump. The brown oil, N1,N3-di(2-methoxyphenyl)-2,2-dichloropropanediimidoyl dichloride, was not further purified.

At room temperature 15.4 mmol sodium azide was added to a solution of 1.61 mmol N1,N3-di(2-methoxyphenyl)-2,2-dichloropropanediimidoyl dichloride in 5 mL acetone. The reaction was stirred at room temperature for 1 hour. The reaction was diluted with water (50 mL) and extracted with dichloromethane (2×50 mL). The combined extracts were dried ($Na_2SO_4$), filtered, and evaporated to dryness in vacuo to afford the product as a yellow oil. The product was purified by column chromatography (EtOAc/heptane: 1/20 to 1/5) to afford 5-dichloro[1-(2-methoxyphenyl)-1H-1,2,3,4-tetraazol-5-yl]methyl-1-(2-methoxyphenyl)-1H-1,2,3,4-tetraazole in a yield of 239 mg (34%).

$^1$H-NMR (400 MHz, DMSO-d6) δ 3.78 (s, 6H), 6.89 (dd, J=1.5 Hz, J=7.8 Hz, 2H), 7.00-7.05 (m, 2H), 7.13-7.16 (m, 2H), 7.23-7.26 (m, 2H).

LCMS-UV M=433.3 g/mol

1b. Bis-(1-(2,5-dimethylbenzene-5-tetrazolyl)-dichloromethane 100 mmol 2,5-dimethylaniline and 50 mmol diethyl malonate were put together and stirred overnight at 170° C. The formed ethanol was distilled off directly (100 mmol,≡6.6 mL) on a stream of nitrogen. N1,N3-di(2,5-dimethyl-phenyl)-malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 14.9 g N1,N3-di(2,5-dimethyl-phenyl)-malonamide was obtained (yield 96.0%, purity 98.5%)

To a solution of 10 mmol N1,N3-di(2,5-dimethyl-phenyl)-malonamide in 120 mL toluene finely grounded $PCl_5$ (4.5 eq., 45 mmol, 9.37 g) was added portion wise at 50° C. The solution was heated to reflux. If not all material dissolved upon heating more toluene and $PCl_5$ were added in ratio. Reflux was continued for 4-6 hours until gas emission stopped. Then, the solvent was evaporated, after standard distillation of $POCl_3$ and toluene, an oil pump and an oil bath at 140-150° C. were used to remove all volatiles and the (crystalline) residue was washed with cold ethanol. The crystalline mass was filtered and washed on the filter with ethanol to yield 1.54 g of N1,N3-di(2,5-dimethylphenyl)-2,2-dichloropropanediimidoyl dichloride (crude product), dried on a stream of air (yield 37.0%).

1.54 g of N1,N3-di(2,5-dimethylphenyl)-2,2-dichloropropanediimidoyl dichloride was dissolved in 43 mL acetone and the solution was cooled in an ice bath. 2.41 g sodium azide was added and the solution was stirred over weekend at room temperature. A precipitate was formed. 5-dichloro[1-(2,5-dimethylphenyl)-1H-1,2,3,4-tetraazol-5-yl]methyl-1-(2,5-dimethylphenyl)-1H-1,2,3,4-tetraazole was isolated by adding water (approx. 28 mL/g starting material) and filtration. The product was washed with water, dried on an air stream, and recrystallized from EtOH (20 mL/g crude product) to yield 220 mg (yield 13.9%, purity >94%).

1H-NMR (DMSO-d6, 400 MHz) δ 1.75 (s, 6H), 2.25 (s, 6H), 7.00 (s, 2H), 7.35-7.39 (m, 4H)

LCMS-UV M=429.4 g/mol

Melting point=217° C. (decomposition)

1c. Bis-(1-o,m-dichlorobenzene-5-tetrazolyl)-dichloromethane 100 mmol 2,3-dichloroaniline and 50 mmol diethyl malonate were put together and stirred at overnight 170° C. The formed ethanol was distilled off directly (100 mmol≡6.6 mL) on a stream of nitrogen. N1,N3-di(2,3-dichloro-phenyl)-malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 14.7 g N1,N3-di(2,3-dichloro-phenyl)-malonamide was obtained (yield 75.0%, purity 98.4%)

At room temperature, 5 mL $POCl_3$ was added to a mixture of 1.61 mmol N,N'-Bis-(2,3-dichloro-phenyl)-malonamide and 7.54 mmol $PCl_5$. The reaction was heated at reflux for 18 hours. The reaction mixture was evaporated to dryness in vacuo to afford a yellow oil. The crude product was purified by flash column chromatography (EtOAc/heptane: 1/20) to afford N1,N3-di(2,3-dichlorophenyl)-2,2-dichloropropanediimidoyl dichloride as a yellow oil in a yield of 493 mg.

At room temperature 10 mmol sodium azide was added to a solution of 0.99 mmol N1,N3-di(2,3-dichlorophenyl)-2,2-dichloropropanediimidoyl dichloride in 5 mL acetone. The reaction was stirred at room temperature for 3 hours. The reaction was diluted with water (50 mL) and extracted with dichloromethane (50 mL). The organic layer was dried ($Na_2SO_4$), filtered, and evaporated to dryness in vacuo to afford the product as a yellow solid in a yield of 452 mg. The product was purified by flash column chromatography (EtOAc/heptane: 1/100 to 1/4) to afford 340 mg 5-dichloro [1-(2,3-dichlorophenyl)-1H-1,2,3,4-tetraazol-5-yl]methyl-1-(2,3-dichlorophenyl)-1H-1,2,3,4-tetraazole.

$^1$H-NMR (CDCl₃, 400 MHz) δ 7.36-7.41 (m, 2H), 7.46-7.49 (m, 2H), 7.71-7.75 (m, 2H)

LCMS-UV M=510.9 g/mol

Melting point=194° C. (decomposition)

1d. Bis-(1-o-fluorobenzene-5-tetrazolyl)-dichloromethane 100 mmol 2-fluoroaniline and 50 mmol diethyl malonate were put together and stirred overnight at 170° C. The formed ethanol was distilled off directly (100 mmol≡6.6 mL) on a stream of nitrogen. N1,N3-di(2-fluoro-phenyl)-malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 9.9 g N1,N3-di(2-fluoro-phenyl)-malonamide was obtained (yield 68.2%, purity 99.3%)

At room temperature 7.11 mmol $PCl_5$ was added to a suspension of 1.78 mmol N1,N3-di(2-fluoro-phenyl)-malonamide in 5 mL $POCl_3$. The reaction was heated at reflux for 42 hours. The progress of the reaction was monitored using NMR. The reaction mixture was evaporated to dryness in vacuo to afford a yellow oil. The crude product was purified by flash column chromatography (EtOAc/heptane: 1/20). 56 mg N1,N3-di(2-fluorophenyl)-2,2-dichloropropanediimidoyl dichloride was isolated from the column.

At room temperature 2.3 mmol sodium azide was added to a solution of 0.14 mmol N1,N3-di(2-fluorophenyl)-2,2-dichloropropanediimidoyl dichloride in 2 mL acetone. The reaction was stirred at room temperature for 1 hour. The reaction was diluted with water and extracted with dichloromethane. The organic layer was dried ($Na_2SO_4$), filtered, and evaporated to dryness in vacuo to afford a product as a white solid in a yield of 45 mg. The product was purified by flash column chromatography (EtOAc/heptane: 1/100 to 1/2) and thereafter triturated with diisopropyl ether to afford 5-dichloro[1-(2-fluorophenyl)-1H-1,2,3,4-tetraazol-5-yl]methyl-1-(2-fluorophenyl)-1H-1,2,3,4-tetraazole as a white solid in a yield of 17 mg.

$^1$H-NMR ($CDCl_3$, 400 MHz) δ 7.25-7.32 (m, 2H), 7.37-7.42 (m, 2H), 7.59-7.65 (m, 2H)

LCMS-UV M=409.2.9 g/mol

1e. Bis-(1-m-methylbenzene-5-tetrazolyl)-dichloromethane 100 mmol m-toluidine and 50 mmol diethyl malonate were put together and stirred overnight at 170° C. The formed ethanol was distilled off directly (100 mmol≡6.6 mL) on a stream of nitrogen. N1,N3-di(3-methylphenyl)malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 9.5 g N1,N3-di(3-methylphenyl)malonamide (yield 67.3%, purity 97.2%) was obtained.

To a solution of 10 mmol N1,N3-di(3-methylphenyl)malonamide in 120 mL toluene finely grounded $PCl_5$ (4.5 eq., 45 mmol, 9.37 g) was added portion wise at 50° C. The solution was heated to reflux. If not all material dissolved upon heating more toluene and $PCl_5$ were added in ratio. Reflux was continued for 4-6 hours until gas emission stopped. Then, the solvent was evaporated, and after usual distillation of $POCl_3$ and toluene, a oil pump and a oil bath at 140-150° C. were used to remove all volatiles and the (crystalline) residue was washed with cold ethanol. The crystalline mass was filtered and washed on the filter with ethanol to yield 0.52 g of N1,N3-di(3-methylphenyl)-2,2-dichloropropanediimidoyl dichloride (crude product), dried on a stream of air (yield 13.4%).

0.52 g of N1,N3-di(3-methylphenyl)-2,2-dichloropropanediimidoyl dichloride was dissolved in 14.6 mL acetone and the solution was cooled in an ice bath. 0.87 g sodium azide was added and the solution was stirred at room temperature over weekend. A precipitate was formed. 5-dichloro[1-(3-methylphenyl)-1H-1,2,3,4-tetraazol-5-yl]methyl-1-(3-methylphenyl)-1H-1,2,3,4-tetraazole was isolated by adding water (approx. 28 mL/g starting material) and filtration. The product was washed with water, dried on an air stream, and recrystallized from EtOH (20 mL/g crude product) to yield 199 mg (yield 37.0%, purity >95%).

$^1$H-NMR (DMSO-d6, 400 MHz) δ 2.36 (s, 6H), 7.18-7.23 (m, 4H), 7.45-7.50 (m, 4H)

LCMS-UV M=401.4 g/mol

1f. Bis-(1-m-chloro-p-methoxybenzene-5-tetrazolyl)-dichloromethane 100 mmol 3-chloro-p-anisidine and 50 mmol diethyl malonate were put together and stirred overnight at 170° C. The formed ethanol was distilled off directly (100 mmol≡6.6 mL) on a stream of nitrogen. N1,N3-di(3-chloro-4-methoxyphenyl)malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 18.1 g N1,N3-di(3-chloro-4-methoxyphenyl)malonamide was obtained (yield 94.5%, purity 99.3%)

At room temperature 5 mL $POCl_3$ was added to a mixture of 1.84 N1,N3-di(3-chloro-4-methoxyphenyl)malonamide and 9.17 mmol $PCl_5$. The reaction was heated at reflux for 18 hours. The reaction mixture was evaporated to dryness in vacuo to afford a yellow oil. The crude product was purified by flash column chromatography (EtOAc/heptane: 1/20 to 1/4) to afford N1,N3-di(3-chloro-4-methoxyphenyl)-2,2-dichloropropanediimidoyl dichloride as a yellow oil in a yield of 281 mg (31%).

At room temperature 5.75 mmol sodium azide was added to a solution of 0.575 mmol N1,N3-di(3-chloro-4-methoxyphenyl)-2,2-dichloropropanediimidoyl dichloride in 5 mL acetone. The reaction was stirred at room temperature for 2 hours. The reaction was diluted with water and the precipitate was filtered to yield 220 mg 1-(3-chloro-4-methoxyphenyl)-5-dichloro[1-(3-chloro-4-methoxyphenyl)-1H-1,2,3,4-tetraazol-5-yl]methyl-1H-1,2,3,4-tetraazole (76%).

$^1$H-NMR (400 MHz, DMSO-d6) δ 3.96 (s, 6H), 7.24 (d, J=8.8 Hz, 2H), 7.49 (dd, J=2.5 Hz, 8.8 Hz, 2H), 7.73 (d, J=2.5 Hz, 2H).

LCMS-UV M=502.2 g/mol

Melting point=167° C. (decomposition)

1g. Bis-(1-(5-chloro-2-methoxybenzene-5-tetrazolyl)-dichloromethane 100 mmol 3-chloro-o-anisidine and 50 mmol diethyl malonate were put together and stirred overnight at 170° C. The formed ethanol was distilled off directly (100 mmol≡6.6 mL) on a stream of nitrogen. N1,N3-di(3-chloro-2-methoxyphenyl)malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 13.2 g N1,N3-di(3-chloro-2-methoxyphenyl)malonamide was obtained (yield 74.9%, purity 98.6%)

20.8 mmol of $PCl_5$ was put in a closed flask and then 4.1 mmol yellowish N1,N3-di(3-chloro-2-methoxyphenyl)malonamide was added under nitrogen atmosphere. 161 mmol POCl₃ was added and N1,N3-di(3-chloro-2-methoxyphenyl)malonamide slowly dissolved while increasing the temperature from room temperature to 110° C. and then stirred for 16 hours. The reaction mixture was cooled, and then concentrated in vacuo. The residue was subjected to flash column chromatography (silica ~50 g, n-heptane (A)/EtOAc (B); 0% B→25% B in 30 min) to yield N1,N3-di(3-chloro-2-methoxyphenyl)-2,2-dichloropropanediimidoyl dichloride.

At room temperature 26.0 mmol sodium azide was added to a solution of 2.54 mmol N1,N3-di(3-chloro-2-methoxyphenyl)-2,2-dichloropropanediimidoyl dichloride in 8.5 mL acetone. The reaction mixture was stirred at room temperature for 1.5 hours. The reaction mixture was diluted with water (50 mL). The precipitate was collected by filtration to afford 1-(3-chloro-2-methoxyphenyl)-5-dichloro[1-(3-chloro-2-methoxyphenyl)-1H-1,2,3,4-tetraazol-5-yl]methyl-1H-1,2,3,4-tetraazole as a pink solid in a yield of 855 mg (67%).

¹H-NMR (400 MHz, DMSO-d6) δ 3.65 (s, 6H), 7.36-7.42 (m, 4H), 7.88 (dd, J=2.0 Hz, J=7.6 Hz, 2H).

LCMS-UV M=502.2 g/mol

Melting point=161° C. (decomposition)

1h. Bis-(1-m,p-dimethylbenzene-5-tetrazolyl)-dichloromethane 100 mmol 3,4-dimethylaniline and 50 mmol diethyl malonate were put together and stirred overnight at 170° C. The formed ethanol was distilled off directly (100 mmol≡6.6 mL) on a stream of nitrogen. N1,N3-di(3,4-dimethylphenyl)malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 13.9 g N1,N3-di(3,4-dimethylphenyl)malonamide was obtained (yield 89.6%, purity 98.5%)

22.4 mmol PCl₅ was put in a closed flask, weighed, and then 4.5 mmol dull orange N1,N3-di(3,4-dimethylphenyl)malonamide was added under nitrogen atmosphere. 161 mmol POCl₃ was added and the N1,N3-di(3,4-dimethylphenyl)malonamide was slowly dissolved while increasing the temperature from room temperature to 110° C. and stirred for 16 hours. The reaction mixture was cooled, and then concentrated in vacuo. The residue was subjected to flash column chromatography (silica ~40 g, n-heptane (A)/EtOAc (B); 0% B→25% B in 30 min) to yield N1,N3-di(3,4-dimethylphenyl)-2,2-dichloropropanediimidoyl dichloride.

4.6 mmol N1,N3-di(3,4-dimethylphenyl)-2,2-dichloropropanediimidoyl dichloride was dissolved in 15 mL acetone while heating. The solution was allowed to cool under argon atmosphere; then, 46.0 mmol sodium azide was added at room temperature and stirred. After 1.5 hours of reaction time, water (100 mL) was added and the mixture was stirred vigorously for ~10 minutes. The solid material was filtered (filtrate was hazy), washed with water, and dried on filter by air current. 750 mg of the product was purified by flash column chromatography (EtOAc/heptane: 1/100 to 1/5) to afford 5-dichloro [1-(3,4-dimethylphenyl)-1H-1,2,3,4-tetraazol-5-yl]methyl-1-(3,4-dimethylphenyl)-1H-1,2,3,4-tetraazole as a yellow solid.

¹H-NMR (DMSO-d6, 400 MHz): δ 2.24 (s, 3H), 2.26 (s, 3H), 6.81 (dd, J=1.9 Hz, J=7.9 Hz, 2H), 6.88 (d, J=1.9 Hz, 2H), 7.25 (d, J=7.9 Hz, 2H).

LCMS-UV M 429.3 g/mol

Melting point=102° C.

1i. Bis-(1-p-phenoxybenzene-5-tetrazolyl)-dichloromethane 100 mmol 4-phenoxyaniline and 50 mmol diethyl malonate were put together and stirred overnight at 170° C. The formed ethanol was distilled off directly (100 mmol≡6.6 mL) on a stream of nitrogen. N1,N3-di(4-phenoxyphenyl)malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 20.6 g N1,N3-di(4-phenoxyphenyl)malonamide was obtained (yield 94.0%, purity 100.0%)

21.8 mmol PCl₅ was put in a closed flask, weighed, and then 4.4 mmol light grey N1,N3-di(4-phenoxyphenyl)malonamide was added under nitrogen atmosphere. 161 mmol POCl₃ was added and a thick, bright yellow paste resulted while increasing the temperature from room temperature to 110° C. for 16 hours. The reaction mixture was cooled, and then concentrated in vacuo. The residue was subjected to flash column chromatography (silica ~40 g, n-heptane (A)/EtOAc (B); 0% B→25% B in 30 min) to yield N1,N3-di(4-phenoxyphenyl)-2,2-dichloropropanediimidoyl dichloride.

At room temperature 46.0 mmol sodium azide was added to a solution of 4.48 mmol N1,N3-di(4-phenoxyphenyl)-2,2-dichloropropanediimidoyl dichloride in 15 mL acetone. The reaction was stirred at room temperature for 1.5 hours. The reaction was diluted with water (50 mL). The aqueous layer was extracted with dichloromethane (50 mL). The organic extract was dried (Na₂SO₄), filtered, and evaporated to dryness in vacuo to afford the product. The product was purified by column chromatography (EtOAc/heptane: 1/100 to 1/5) to afford 1.47 g 5-dichloro [1-(4-phenoxyphenyl)-1H-1,2,3,4-tetraazol-5-yl]methyl-1-(4-phenoxyphenyl)-1H-1,2,3,4-tetraazole (59%).

¹H-NMR (400 MHz, DMSO-d6) δ 7.06-7.13 (m, 8H), 7.18-7.22 (m, 6H), 7.41-7.46 (m, 4H).

LCMS-UV M=557.4 g/mol

1j. Bis-(1-(3-chloro-2-methoxybenzene-5-tetrazolyl)-dichloromethane 100 mmol 5-chloro-o-anisidine and 50 mmol diethyl malonate were put together and stirred overnight at 170° C. The formed ethanol was distilled of directly (100 mmol≡6.6 mL) on a stream of nitrogen. N1,N3-di(5-chloro-2-methoxyphenyl)malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 16.0 g N1,N3-di(5-chloro-2-methoxyphenyl)malonamide was obtained (yield 84%, purity 100%)

At room temperature 5 mL POCl₃ was added to a mixture of 1.33 mmol N1,N3-di(5-chloro-2-methoxyphenyl)malonamide and 7.49 mmol PCl₅. The reaction was heated at reflux for 18 hours. The reaction mixture was evaporated to dryness in vacuo to afford a yellow oil. The crude product was purified by flash column chromatography (EtOAc/heptane: 1/20 to 1/3) to afford N1,N3-di(5-chloro-2-methoxyphenyl)-2,2-dichloropropanediimidoyl dichloride as a yellow oil in a yield of 293 mg (45%).

At room temperature 6.0 mmol sodium azide was added to a solution of 0.6 mmol N1,N3-di(5-chloro-2-methoxyphenyl)-2,2-dichloropropanediimidoyl dichloride in 3 mL acetone. The reaction was stirred at room temperature for 1.5 hours. The reaction was diluted with water (50 mL), the precipitate was filtered and yielded 221 mg 1-(5-chloro-2-methoxyphenyl)-5-dichloro[1-(5-chloro-2-methoxyphenyl)-1H-1,2,3,4-tetraazol-5-yl]methyl-1H-1,2,3,4-tetraazole.

$^1$H-NMR (DMSO-d6, 400 MHz) δ 3.61 (s, 6H), 7.31 (d, J=9.1 Hz, 2H), 7.40-765 (m, 2H), 7.75-7.79 (m, 2H).

LCMS-UV M=502.2 g/mol

Melting point=246° C. (decomposition)

1k. Bis-(1-o-tolyl-5-tetrazolyl)-dichloromethane 329 mmol o-toluidine and 165 mmol diethyl malonate were put together and stirred overnight at 170° C. The formed ethanol was distilled off directly on a stream of nitrogen. N1,N3-di(2-methylphenyl)malonamide was formed as one solid block. The reaction was cooled and EtOAc was added. The product had to be crushed with a mortar, because it resembled very hard brick. The crushed material was stirred in EtOAc and filtered. EtOAc added was added twice and the mixture was stirred and filtered each time. 38.1 g N1,N3-di(2-methylphenyl) malonamide (yield 82%) was obtained.

To a solution of 10.6 mmol N1,N3-di(2-methylphenyl) malonamide in 127 mL toluene 48.0 mmol finely grounded $PCl_5$ was added portion wise. The reaction mixture was heated and refluxed for 4-6 hours. The reaction mixture was evaporated to dryness in vacuo. The residue was evaporated with toluene twice to afford N1,N3-di(2-methylphenyl)-2,2-dichloropropane diimidoyl dichloride in a yield of 1.79 g. The crude product was used as such in follow-up experiment.

4.61 mmol crude N1,N3-di(2-methylphenyl)-2,2-dichloropropane diimidoyl dichloride was dissolved in 50 mL acetone and cooled in an ice bath. 46.1 mmol sodium azide was added and the reaction mixture was stirred at room temperature over the weekend. The product was isolated by adding water (approx. 50 mL) and filtration. The material was washed with water and dried in an air stream to yield 1.4 g 5-dichloro[1-(2-methylphenyl)-1H-1,2,3,4-tetraazol-5-yl]methyl-1-(2-methylphenyl)-1H-1,2,3,4-tetraazole (80%).

$^1$H-NMR (400 MHz, CDCl$_3$) δ 1.80 (bs, 6H), 7.29-7.34 (m, 2H), 7.37-7.42 (m, 2H), 7.47-7.50 (m, 2H), 7.55-7.60 (m, 2H).

LCMS-UV M=401.3 g/mol

1l. Bis-(1-o-tolyl-5-tetrazolyl)-chloromethane

The synthesis was performed under argon atmosphere. 0.2 mmol 5-dichloro[1-(2-methylphenyl)-1H-1,2,3,4-tetraazol-5-yl]methyl-1-(2-methylphenyl)-1H-1,2,3,4-tetraazole (as produced in example 1k) was dissolved in 5 mL acetonitrile. 0.4 mmol triethylamine (56.2 µl; 0.4 mmol) and 0.20 malonodinitrile was added to the reaction mixture and stirred at room temperature for 16 hours. The reaction mixture was evaporated to dryness in vacuo and the crude product was purified by flash column chromatography (EtOAc/heptane: 1/100 to 1/3) to afford a product as a white solid in a yield of 110 mg. The product contains heptane and was therefore dried in vacuum oven at 40° C. to afford 5-chloro[1-(2-methylphenyl)-1H-1,2,3,4-tetraazol-5-yl]methyl-1-(2-methylphenyl)-1H-1,2,3,4-tetraazole in a yield of 56 mg (60%).

1H-NMR (400 MHz, DMSO-d6) δ 1.83 (s, 6H), 7.02 (s, 1H), 7.26 (bs, 2H), 7.41-7.46 (m, 2H), 7.48-7.51 (m, 2H), 7.56-7.61 (m, 2H).

LCMS-UV M=366.8 g/mol

1m. Synthesis of Tetrazolyl Monochloromethanes

Analogous to example 11, wherein the dichloro-compound NewCo003 was converted to its monochloromethane derivative (NewCo0030) all the dichloro compounds of Table 1 can be converted to their monochloric pendants.

Example 2

MIC Tests

MIC test were performed according to standard methodology: M7-A6-"Methods for Dilution Antimicrobial Susceptibility Tests for Bacteria That Grow Aerobically"; *Approved Standard*, Sixth Edition Clinical and Laboratory Standards Institute 2005 (CLSI/formerly NCCLS).

Table II lists the results of 6 different compounds according to Formula (I) on single strains of *S. aureus* as MIC values expressed in micrograms per milliliter.

From this list it appears that BAS 00160352 (NewCo003, Bis-(1-o-tolyl-5-tetrazolyl)-dichloromethane) is the most active compound.

Table III lists the results of experiments on multiple strains of *S. aureus*. The MIC values are expressed as a range between the lowest value and the highest value found in these experiments. Both the average MIC50 and MIC90 are indicated in bold. Again BAS 00160352 is found to be the most active. For comparison a positive control (vancomycin) has been tested.

Table IV lists additional MIC data on single strains of *S. aureus* as MIC values expressed in micrograms per milliliter. Again BAS 00160352 (NewCo003) is tested, next to its monochloric pendant (NewCo0030) and several of the new compounds of Table I. Some of the experiments were carried out in duplicate. Strains TTC03.0236 and TTC03.0239 are two MRSA strains obtained from the Utrecht University Medical Centre (UMC 01-8756/140 and UMC 03-543155, respectively). Several of the new compounds of Table I appear to be at least as active as NewCo003.

TABLE II

| | | MIC DETERMINATION SINGLE STRAINS | | |
|---|---|---|---|---|
| IDNumber | CAS | S. aureus ATCC 29213 | S. aureus MW2 | S. aureus N315 |
| NewCo003 | 105678-65-7 | 0.06 | 0.06 | 0.125 |
| NewCo002 | 77174-39-1 | >32 | >32 | 4 |
| NewCo001 | 105678-80-6 | 16 | 32 | 2 |
| NewCo004 | 77166-08-6 | 1 | 1 | 0.25 |
| NewCo006 | 105678-79-3 | 4 | | |
| NewCo005 | 138352-04-2 | 4 | | |

TABLE III

| Compound | No of tested S. aureus strains. | Range MIC (lowest-highest) (microgram/milliliter) | MIC 50 | MIC 90 |
|---|---|---|---|---|
| NewCo003 | 60 | 0.03 0.5 | 0.06 | 0.12 |
| NewCo002 | 60 | 0.5 >32 | 32 | >32 |
| NewCo001 | 60 | 1 >32 | 4 | 16 |
| NewCo004 | 60 | 0.25 4 | 1 | 2 |
| vancomycin | 60 | 0.12 4 | 0.5 | 1 |

TABLE IV

MIC DETERMINATION SINGLE STRAINS

| IDNumber | CAS | S. aureus TTC03.0236 | | S. aureus TTC03.0239 | | S. aureus ATCC 29213 | |
|---|---|---|---|---|---|---|---|
| vancomycine | | 0.39 | ≦0.05 | 1.56 | 3.125 | 1.56 | 0.78 |
| NewCo003 | 105678-65-7 | 0.19 | ≦0.05 | 0.39 | ≦0.05 | 0.19 | 0.1 |
| NewCo0030 | | 0.19 | ≦0.05 | 0.19 | ≦0.05 | 0.19 | ≦0.05 |
| NewCo0018 | | 0.78 | 0.78 | 6.25 | 1.56 | 1.56 | 1.56 |
| NewCo009 | | 0.39 | 0.1 | 1.56 | 0.39 | 0.78 | 0.19 |
| NewCo007 | | 1.56 | | 1.56 | | 1.56 | |
| NewCo0021 | | 0.78 | | 1.56 | | 1.56 | |
| NewCo0022 | | 0.1 | | 0.19 | | ≦0.05 | |
| NewCo0023 | | 0.19 | | 0.39 | | 0.19 | |

Example 3

In Vivo Toxicity Test

The purpose of this study was to investigate the antibiotic efficacy of different doses of compound BAS00160352 (NewCo003) against a local infection with MRSA 2141 in the mouse. Thirty mice were treated intravenously with 0.05, 0.5 or 5.0 mg/kg body weight, respectively. Outgrowth of the infection was used to establish drug efficacy.

For each administered dose the appropriate stock solution was made as a 1 ml aliquot of the test substance in the vehicle (DMSO). The stock solutions were stored at 2-8° C. for 16 hours.

Positive control: Vancomycin (Vancomycine 500 PCH, vancomycinehydrochloride voor i.v. gebruik, chargenr. 03L19A, expiry date: November 2005, Pharmachemie, Haarlem, The Netherlands)

| Animals and housing conditions | |
|---|---|
| Species: | mouse |
| Strain: | Swiss out bred (IcoCaw OF1) |
| Supplier: | Charles River Nederland, The Netherlands |
| Sex and age: | 50 female, 6-8 weeks old upon arrival |
| Identification: | individually markings on the tail |
| Acclimatization period: | 7 days |
| Caging: | 5 animals/sex per cage (Macrolon cages with filter top and environmental enrichment: shreds of paper. |
| Handling: | mice were handled under laminar flow |
| Lighting: | 12 hour light/12 hour dark cycle |
| Temperature during testing: | 22 ± 3° C. |
| Humidity during testing: | 30%-70% |
| Ventilation: | ca 10 air changes/hour |
| Diet: | food and water ad libitum; SDS D3 food (Special Diets Service, Witham, England) |

Administration of the Test Substance

The test substances were administered as a solution in dimethylsulfoxide (DMSO). The test substance was administered as 20 µl injections per mouse at all dose levels. Vancomycin was used as positive control and injected intravenously as a 10 mg/ml solution in DMSO (20 µl per mouse). Fresh dilutions of the test substance in vehicle were provided, stored at 2-8° C., and used within 18 hours after preparation. Shortly before injection the test substance was warmed to room temperature.

Study design and Dose Levels

The mice were injected i.m. with 22E05 MRSA 2141 bacteria, strain 2141 in the right thigh muscle, followed one day later by an i.v. injection of the test compound, vancomycin or vehicle in the tail vein. 24 hours later mice were sacrificed, blood was collected by heart puncture and the right thigh muscle was removed. Plasma was prepared from blood samples and stored at −80°±10° C. for possible future analysis. Thigh muscles were weighted and homogenized using an Ultra-Turrax® and dilutions of the homogenate were prepared in saline. Limiting dilutions were plated onto agar plates and two days later the number of MRSA 2141 CFU were determined for each individual mouse as an indication of bactericidal activity of the compound. Additionally, tests were performed to determine if the bacteria used are still oxacillin resistant *Staphylococcus aureus*. This was done before injection and on pooled thigh muscle isolates per group. For this purpose Staphaurex® (Remel Europe Ltd., Crossways, UK) and ORSAB®+supplements (Oxoid Ltd., Basingstoke, UK) were used. In vivo antibiotic activity is determined by a CFU reduction of >90% (1 log reduction) in comparison to the negative control (vehicle only).

Dose Levels

The study comprised five groups of 10 females each.
The groups are presented in Table V:

TABLE V

| Group | Dose levels (mg/kg body weight)[1] | Concentration (mg/ml) | Dose volume (ml/kg) | Number of mice (♀) |
|---|---|---|---|---|
| A 0[1] | 0 | 0 | 1 | 10 |
| B 0.05 | 0.05 | 0.05 | 1 | 10 |
| C 0.5 | 0.5 | 0.5 | 1 | 10 |
| D 5 | 5 | 5 | 1 | 10 |
| E vanco | 10 | 10 | 1 | 10 |

[1]vehicle only (DMSO)

In Vivo Effect of Single Dose of Compound BAS00160352

The results of the in vivo data from the experiment are presented in FIG. 1 and show:
1. Bacterial outgrowth in mice that received vehicle (DMSO) only
2. Over 1 Log reduction in the population treated with vancomycin (positive control)
3. Approximately 2 Log reduction in the groups treated with the test substances.

A statistical analysis (using GraphPad Prism (V3) of the experimental data shows that the compound BAS00160352 was effective (P≦0.001) against a local MRSA 2141 infection. Individual analysis of the compound at different doses against the untreated group indicate that significant reduction of bacterial outgrowth was achieved by the compound at 0.05 mg/kg (P≦0.01), 0.5 mg/kg (P≦0.01) and 5.0 mg/kg (P≦0.01) doses, and no significant trend of dose-dependent efficacy was observed.

During observation after injection no signs of adverse side effects were observed.

The invention claimed is:

1. A pharmaceutical composition comprising a compound according to formula (I)

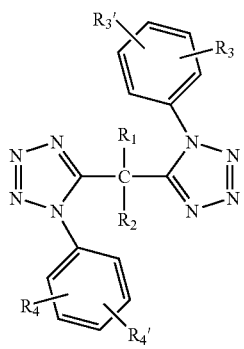

Wherein $R_1$ and $R_2$ are each independently halogen, lower alkyl or absent, with the proviso that $R_1$ and $R_2$ are not both absent, and wherein $R_3$, $R_{3'}$, $R_4$ and $R_{4'}$ are each independently absent, OH, $SO_2NH_3$, lower alkyl, lower alkoxy, lower alkoxy (methyl), aryl, heteroaryl, wherein lower alky, aryl and heteroaryl may be substituted, arylalkoxy or halogen.

2. A pharmaceutical composition according to claim 1, wherein either $R_1$ or $R_2$ or both are Cl.

3. A pharmaceutical composition according to claim 1, wherein $R_{3'}$, and $R_{4'}$, are absent and $R_3$ or $R_4$ or both are linked to the phenyl moiety at the ortho position.

4. A pharmaceutical composition according to any one of the above mentioned claims, wherein $R_3$ and/or $R_4$ are selected from the group comprising $CH_3$, Cl, or $O$—$CH_3$.

5. A pharmaceutical composition comprising a compound according to formula (I) or a pharmaceutically acceptable salt, prodrug, ester or solvate thereof and a pharmaceutically acceptable carrier.

6. A method of treating a bacterial infection comprising administering a compound according to formula (I) or a pharmaceutically acceptable salt, prodrug, ester or solvate thereof.

* * * * *